US006906108B2

(12) United States Patent
Henderson et al.

(10) Patent No.: US 6,906,108 B2
(45) Date of Patent: Jun. 14, 2005

(54) EXTRACTS OF VETIVER OIL AS REPELLENT AND TOXICANT TO ANTS, TICKS, AND COCKROACHES

(75) Inventors: Gregg Henderson, Saint Gabriel, LA (US); Donald O. Heumann, Metairie, LA (US); Roger A. Laine, Baton Rouge, LA (US); Lara Maistrello, Baton Rouge, LA (US); Betty C. R. Zhu, Baton Rouge, LA (US); Feng Chen, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 85 days.

(21) Appl. No.: 09/932,555

(22) Filed: Aug. 17, 2001

(65) Prior Publication Data

US 2003/0073748 A1 Apr. 17, 2003

(51) Int. Cl.$^7$ ...................... A61K 31/12; A61K 31/045; A61K 31/015; A01N 27/00

(52) U.S. Cl. ........................ 514/691; 514/729; 514/766

(58) Field of Search ............................... 514/691, 729, 514/766, 683

(56) References Cited

U.S. PATENT DOCUMENTS

| | | | |
|---|---|---|---|
| 3,835,192 A | 9/1974 | Van Der Linde et al. | 260/586 R |
| 4,933,371 A | 6/1990 | Hink et al. | 514/739 |
| 4,937,073 A | 6/1990 | Fujikura et al. | 424/195.1 |
| 5,227,163 A | 7/1993 | Eini et al. | 424/195.1 |
| 5,411,992 A | 5/1995 | Eini et al. | 514/731 |
| 5,591,435 A | 1/1997 | Vaccarello-Dunkel et al. | 424/195.1 |
| 5,696,158 A | 12/1997 | Oliver | 514/463 |
| 5,847,226 A | 12/1998 | Muller et al. | 568/346 |
| 5,874,097 A | 2/1999 | Henderson et al. | 424/405 |
| 5,965,518 A * | 10/1999 | Nakatsu et al. | 512/1 |
| 5,977,186 A | 11/1999 | Franklin | 514/690 |
| 6,130,253 A | 10/2000 | Franklin et al. | 514/690 |
| 6,270,753 B1 * | 8/2001 | Mullen | 424/76.8 |
| 6,548,085 B1 * | 4/2003 | Zobitne et al. | 424/725 |

FOREIGN PATENT DOCUMENTS

| | | |
|---|---|---|
| EP | 1033076 | 9/2000 |
| WO | 01/28343 A1 | 4/2001 |
| WO | 0128343 * | 4/2001 |

OTHER PUBLICATIONS

Maistrello et al, Efficacy of vetiver oil and nootkatone as soil barriers against formosan subterranean termites, 2001, J. of Econ. Entom., vol. 94 No. 6, pp. 1532–1537.*

Andersen, N., "Biogenetic implications of the antipodal sesquiterpenes of vetiver oil," Phytochemistry, vol. 9, pp. 145–151 (1970).

Andersen, N.H., "The structures of zizanol and vetiselinenol," Tetrahedron Letters, vol. 21, pp. 1755–1758 (1970).

Andersen, N.H., et al., "Prezizaene and the biogenesis of zizaene," Chemistry and Industry, pp. 62–63 (1971).

Chen, C. et al., Isolation and identification of 2–phenoxyethanol from a ballpoint pen as a trail–following substance of *Coptotermes formosanus* Shiraki and *Reticulitermes* sp., J. Entomol. Sci., vol. 33, pp. 97–105 (1998).

Chen, J. et al., "Determination of feeding preference of Formosan subterranean termite (*Coptotermes formosanus* Shiraki) for some amino acid additives," J. Chem. Ecol., vol. 23, pp. 2359–2369 (1996).

Chen, J. et al., "Termites fumigate their nests with naphthalene," Nature, vol. 392, pp. 558 (1998).

Coates, R.M. et al., "The crystal structure of khusimol p–bromobenzoate," Chemical Communications, pp. 999–1000 (1969).

Erdtman, H. et al., "The Chemistry of the Natural Order Cupressales XVIII: Nootkatone, a new sesquiterpene type hydrocarbon from the heartwood of *Chamaecyparis nootkatensis* (Lamb.) Spach.," Acta Chem. Scand., vol. 11, pp. 1157–1161 (1957).

Erdtman, H. et al., "The Chemistry of the Natural Order Cupressales 46. The structure of nootkatone", Acta Chem. Scand., vol. 16, pp. 1311–1314 (1962).

Isman, M., "Biopesticides based on phytochemicals," Advances in Biopesticide Research, pp. 1–12 (2000).

Isman, M., "Pesticides based on plant essential oils," Pesticide Outlook, vol. 10, pp. 68–72 (1999).

Jain et al., "Insect Repellents from Vetiver Oil: I. Zizanal and Epizizanal," Tetrahedron Letters, vol. 23, pp. 4639–4642 (1982).

(Continued)

*Primary Examiner*—Alton Pryor
(74) *Attorney, Agent, or Firm*—Bonnie J. Davis; John H. Runnels

(57) ABSTRACT

Extracts of vetiver oil were found to be significant repellents and toxicants of ants, ticks, and cockroaches. Nootkatone was shown to significantly decrease ant invasion and increase mortality in fire ants. Nootkatone is an effective repellent and toxicant of ants either by itself or as an addition to other substrates, including mulches made from vetiver grass roots, diatomaceous earth, alumina, silica, clays; building materials made from either aluminum or wood; and other suitable solid substances. Nootkatone was also a repellent and toxicant to ticks; and a repellent to cockroaches. Nootkatone is non-toxic to humans and other mammals and is environmentally safe. In addition, it is believed that other extracts of vetiver oil, specifically α-cedrene, zizanol and bicyclovetivenol, will be effective against ants, ticks, and cockroaches.

12 Claims, 4 Drawing Sheets

OTHER PUBLICATIONS

Kaiser, R. et al., "Biogenetically significant components in vetiver oil," Tetrahedron Letters, vol. 20, pp. 2009–2012 (1972).

Maistrello, L. et al., "Effects of nootkatone and a borate compound on Formosan subterranean termite and its symbiont protozoa," J. Entomol. Sci. 36(3), pp. 229–236 (Jul. 2001).

Maistrello, L. et al., "Effects of vetiver oil and its consitutents on *Coptotermes formosanus* and its symbiotic fauna," poster presentation at XXI International Congress of Entomology, Iguassu Falls, Brazil, Aug. 20–26, 2000.

Miyazawa, M. et al., "Insecticidal sesquiterpene from *Alpinia oxyphylla* against *Drosophila melanogaster*," J. Agric. Food Chem., vol. 48, pp. 3639–3641 (2000).

Vetiver Grass: A Thin Green Line Against Erosion, Board on Science and Technology for International Development, National Research Council, National Academy Press, Washington, D.C. 171 pp. (1993).

Weyerstahl, P. et al., "New sesquiterpene ethers from vetiver oil," Liebigs Ann., pp. 1195–1199 (1996).

Zhu, B. et al., "Evaluation of vetiver oil and seven-insect-active essential oils against Formosan Subterranean Termites," J. Chem. Ecol., vol. 27(8), pp. 1617–1625 (Aug. 2001).

Zhu, B. et al., "Nootkatone is a repellent for Formosan subterranean termites (*Coptotermes formosanus*;" Journal of Chemical Ecology, vol. 27, pp. 523–531 (2001).

\* cited by examiner

EXTRACTS OF VETIVER OIL AS REPELLENT AND TOXICANT TO ANTS, TICKS, AND COCKROACHES

The development of this invention was partially funded by the Government under grant no: USDA/ARS 58-6435-8-084 from the United States Department of Agriculture. The Government has certain rights in this invention.

This invention pertains to a method to repel certain arthropods, particularly ants (e.g., red-imported fire ants, *Solenopsis invicta*), ticks (e.g., *Ixodes scapularis*), and cockroaches (e.g., the German cockroach, *Blattella germanica*), using certain extracts of vetiver oil, for example nootkatone, α-cedrene, zizanol, and bicyclovetivenol.

Various species of insects pose significant economic and health problems for humans. For example, leaf-cutting ants defoliate citrus trees. In the southern United States, red imported fire ants, *Solenopsis invicta* Buren, pose problems for growing crops, young trees, wildlife, pets, electrical equipment, etc. Fire ants also pose a health threat to people. Many people are stung multiple times by fire ants, and these multiple stings can severely affect those who are allergic to ant stings, especially the very young or the very old. Fire ants belong to the Class Hexapoda, Order Hymenoptera.

The primary control for ants currently involves the use of insecticides. However, insecticides offer only temporary relief due to the high reproductive capacity, the efficient foraging behavior, and the ecological adapatability of ants. Moreover, many insecticides pose a threat to beneficial animals, including birds and mammals. There is a need for a compound that is relatively non-toxic to birds and mammals, but is still effective as a repellent and toxicant to ants.

The search for new repellents or toxicants is difficult because studies have shown that arthropods, particularly insects, display widely differing sensitivities to different chemicals, including many insecticides. For example, although some essential oils have been shown to be toxic or repellent to some kinds of insects, the toxicity of an essential oil to a particular insect pest species, and selectivity among species have been described as idiosyncratic. See M. Isman, "Pesticides based on plant essential oils," Pesticide Outlook, vol. 10, pp. 68–72 (1999). For example, acyl derivatives of phenols from essential oils have been found to be more active against fly eggs than are the parent phenols, but less effective when applied topically to adult flies. Ether derivatives of monoterpenes from essential oils were found to be more effective against some, but not all insect species assayed. See Isman, 1999.

Naphthalene, a toxicant for most insects, was found to be used as a beneficial fumigant by termites for their nests at concentrations that kill another group of insects, the fire ants. See U.S. Pat. No. 5,874,097; and J. Chen et al., "Termites fumigate their nests with naphthalene," Nature, vol. 392, pp. 558 (1998). Moreover, unlike many herbivorous insects, omnivorous insects (e.g., fire ants) may not be affected by many phytochemicals evolved by plants for protection from insect pests. See M. Isman, "Biopesticides based on phytochemicals," Advances in Biopesticide Research, (2000).

The differences in sensitivity to specific chemicals among major insect groups may reflect that these groups have diverged from one another many millions of years ago. The oldest insect fossil known has been dated to be about 400 million years old. One of the most ancient insect groups is the cockroaches, which appeared in the fossil record about 300 million years ago. Termites appeared about 250 million years ago. The hymenopterans, including ants, bees and wasps, appeared about 200 million years ago. Fleas and the dipterans (flies and mosquitos), appeared about 240 million years ago.

Ticks, although belonging to the same phylum as insects, Arthropoda, are more closely related to spiders and mites. Ticks belong to the Class Arachnida and Order Acari. Ticks feed on the blood of mammals, birds, and reptiles. Ticks usually are found on the ends of grass blades until attracted by a host. Host attractants include chemical attractants, e.g., lactic acid and carbon dioxide, and physical movement. Ticks cause several diseases in humans, including spotted fever, relapsing fever, tularemia, Lyme disease, and Texas cattle fever. One of the tick species known to transmit Lyme disease is *Ixodes scapularis*.

Fleas are secondarily wingless insects that belong to the Class Hexapoda and Order Siphonaptera. Fleas feed as adults on the blood of birds and mammals. Fleas have a complete metamorphosis in which the larvae are maggot-like and crawl through carpet or ground material in search for food. In contrast, adult fleas are jumping insects in search of a suitable host. One disease transmitted by fleas is plague.

Cockroaches are one of the oldest groups of insects, having existed for approximately 350 million years. Cockroaches belong to the Class Hexapoda and Order Blatteria. They have an incomplete metamorphosis, in which the young cockroaches look and behave similarly to the adults. Cockroaches are omnivores and will eat almost any human food. German cockroaches, *Blattella germanica*, are the most problematic species of cockroaches in the U.S. Cockroaches are a major cause of asthma in the U.S. and also carry many disease organisms in and on their bodies.

Vetiver grass (*Vetiveria zizanioides*), a fast growing native of India, belongs to the same grass family group that includes maize, rice, wheat, sorghum, sugarcane, and lemongrass. Vetiver is known to grow roots extremely fast and is used to prevent erosion. See Vetiver Grass: A Thin Green Line Against Erosion, Board on Science and Technology for International Development, National Research Council, National Academy Press, Washington, D.C. 171pp. (1993). In India, vetiver roots are woven into mats, baskets, fans, sachets, and ornaments. The woven mats are believed to provide protection from insect pests, in addition to having a pleasant fragrance. Although the dried roots have been used to repel clothes moths, head lice, and bedbugs, termites are known to eat vetiver grass. Sugarcane, a member of the same grass family, is even known to be a preferred food of the Formosan subterranean termite. See Vetiver Grass: A Thin Green Line Against Erosion, p. 63 and 81 (1993); and J. Chen et al., "Determination of feeding preference of Formosan subterranean termite (*Coptotermes formosanus* Shiraki) for some amino acid additives," J. Chem. Ecol., vol. 23, pp. 2359–2369 (1996). It has been speculated that solid bands of vetiver grass may potentially block termites, fire ants, or other underground insects because other insects were known to avoid vetiver oil and vetiver roots. See Vetiver Grass: A Thin Green Line Against Erosion, pp. 24, 28, 80, and 92 (1993).

Vetiver oil extracted from the roots is used in the soap and perfume industry because it has a pleasant and persistent fragrance. See U.S. Pat. No. 4,937,073. Vetiver oil is known to be a complex mixture of over 300 compounds, over 150 of which are sesquiterpenoid compounds. See P. Weyerstahl et al., "New sesquiterpene ethers from vetiver oil," Liebigs Ann., pp. 1195–1199 (1996); N. H. Andersen, "The structures of zizanol and vetiselinenol," Tetrahedron Letters, vol. 21, pp. 1755–58 (1970); R. M. Coates et al., "The crystal structure of khusimol β-bromobenzoate," Chemical Communications, pp. 999–1000 (1969). Vetiver oil is known to repel flies and cockroaches. The ingredients in vetiver oil reported to repel insects are the ketones—α-vetivone, β-vetivone, khusimone; and the aldehydes—zizanal, and epizizanal. See Vetiver Grass: A Thin Green Line Against Erosion, p. 80 and 92 (1993); and Jain et al., "Insect Repellents from Vetiver Oil: I. Zizanal and Epizizanal," Tetrahedron Letters, vol. 23, pp. 4639–4642 (1982). A minor component of vetiver oil was found to be α-cedrene. See R. Kaiser et al., Tetrahedron Letters, vol. 20, pp. 2009–2012 (1972). None of the above references report that an extract of vetiver oil is repellent to fire ants.

Nootkatone, or 4,4a,5,6,7,8-hexahydro-6-isopropenyl-4, 4a-dimethyl-2(3H)-naphthalone, is a mildly pungent sesquiterpene ketone found in the oil of Alaska yellow cedar (Chamaecyparis nootkatensis) and in a great number of citrus oils, especially oil from grapefruit (Citrus pavadisi). Nootkatone is widely used in the perfumery and flavor industries being essentially non-toxic to humans. See U.S. Pat. Nos. 3,835,192 and 5,847,226; H. Erdtman et al., "The Chemistry of the Natural Order Cupressales XVIII: Nootkatone, a new sesquiterpene type hydrocarbon from the heartwood of Chamaecyparis nootkatensis (Lamb.) Spach.," Acta Chem. Scand., vol. 11, pp. 1157 (1957); and H. Erdtman et al., "The Chemistry of the Natural Order Cupressales 46. The structure of nootkatone," Acta Chem. Scand., vol. 16, pp. 1311 (1962). Nootkatone has also been identified as a minor component of vetiver oil. See U.S. Pat. No. 4,937,073; and N. H. Andersen et al., "Prezizaene and the biogenesis of zizaene," Chemistry and Industry, pp. 62–63 (1971); N. Andersen, "Biogenetic implications of the antipodal sesquiterpenes of vetiver oil," Phytochemistry, vol. 9, pp. 145–151 (1970); and R. Kaiser et al., "Biogenetically significant components in vetiver oil," Tetrahedron Letters, vol. 20, pp. 2009–2012 (1972). The structure of nootkatone is shown below:

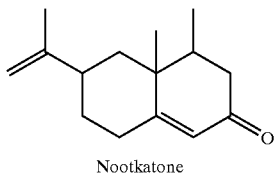

Nootkatone

Nootkatone and epinootkatol, as extracts of the Japanese fruit Alpinia oxyphylla, were recently identified as having insecticidal activity against the larval and adult stages of Drosophila melanogaster. See M. Miyazawa et al., "Insecticidal sesquiterpene from Alpinia oxyphylla against Drosophila melanogaster," J. Agric. Food Chem., vol. 48, pp. 3639–3641 (2000). Flies belong to the Class Hexapoda and Order Diptera.

European Patent Application No. EP 1033076 A1 discloses the use of an aerosol containing nootkatone, valencene or a mixture to repel mosquitos of the genera Culex and Aedes. Mosquitos belong to the arthropod Class Hexapoda and the Order Diptera.

U.S. Pat. Nos. 6,130,253 and 5,977,186 disclose a terpene-based pesticide for killing terrestrial arthropods, including lice, mites, and ants, wherein the terpenes discussed include limnoene, beta-ionone, linalool, geraniol, eugenol, carvone, myrcene, and citral.

U.S. Pat. No. 5,696,158 discloses a repellent composition for lice containing piperonal as a main ingredient.

U.S. Pat. No. 5,591,435 discloses a composition as an insecticide or as an insect behavioraly active composition comprising compounds from aromatic plants, including geranium, balsam root, sage brush, African mint, and horse mint.

U.S. Pat. Nos. 5,411,992 and 5,227,163 disclose lice-repellent compositions comprising terpenoids, especially terpenoid-alcohols, terpenoid-esters, and some aldehydes and ketones of terpenes, excluding the terpene linalool.

U.S. Pat. No. 4,933,371 discloses the use of linalool as apesticide against ticks and fleas.

We have previously found that certain extracts of vetiver oil are effective repellents and toxicants of termites. Termites are in the arthropod Class Hexapoda and Order Isoptera. Although termites and ants may appear similar, the two groups of insects are unrelated. Nootkatone was found to be a component of one of the termite-repelling extracts from the vetiver oil. See B. Zhu et al., "Nootkatone is a repellent for Formosan subterranean termites (Coptotermes formosanus)," Journal of Chemical Ecology, vol. 27, pp. 523–531 (2001); L. Maistrello et al., "Effects of nootkatone and a borate compound on Formosan subterranean termite (Isoptera: Rhinotermitidae) and its symbiont protozoa," J. Entomol. Sci., vol.36, pp.229–236 (2001); B. Zhu et al., "Evaluation of vetiver oil and seven insect-active essential oils against Formosan subterranean termites," J. Chem. Ecol., vol.27, pp.1617–1625 (2001); and L. Maistrello et. al., "Effects of vetiver oil and its consitutents on Coptotermes formosanus and its symbiotic fauna," poster presentation at XXI International Congress of Entomology, Iguassu Falls, Brazil, Aug. 20–26, 2000; and the complete text of the U.S. provisional application, Ser. No. 60/160,251, filed Oct. 19, 1999; and of the international application PCT/US00/29006, filed Oct. 18, 2000; published as WO 01/28343.

We have discovered that certain extracts of vetiver oil are significant repellents and toxicants of ants, ticks, and cockroaches. We have shown that nootkatone significantly decreased ant invasion, and significantly increased mortality in fire ants. Nootkatone is an effective repellent and toxicant of fire ants either by itself or as an addition to other substrates, including mulches made from vetiver grass roots, diatomaceous earth, alumina, silica, clays; building materials made from either aluminum or wood; and other suitable solid substances. Nootkatone was also a repellent and toxicant to ticks; and a repellent to cockroaches. Nootkatone is non-toxic to humans and other mammals and is environmentally safe. In addition, it is believed that other extracts of vetiver oil, specifically α-cedrene, zizanol and bicyclovetivenol, will be effective against ants, ticks, and cockroaches.

Figure 1:
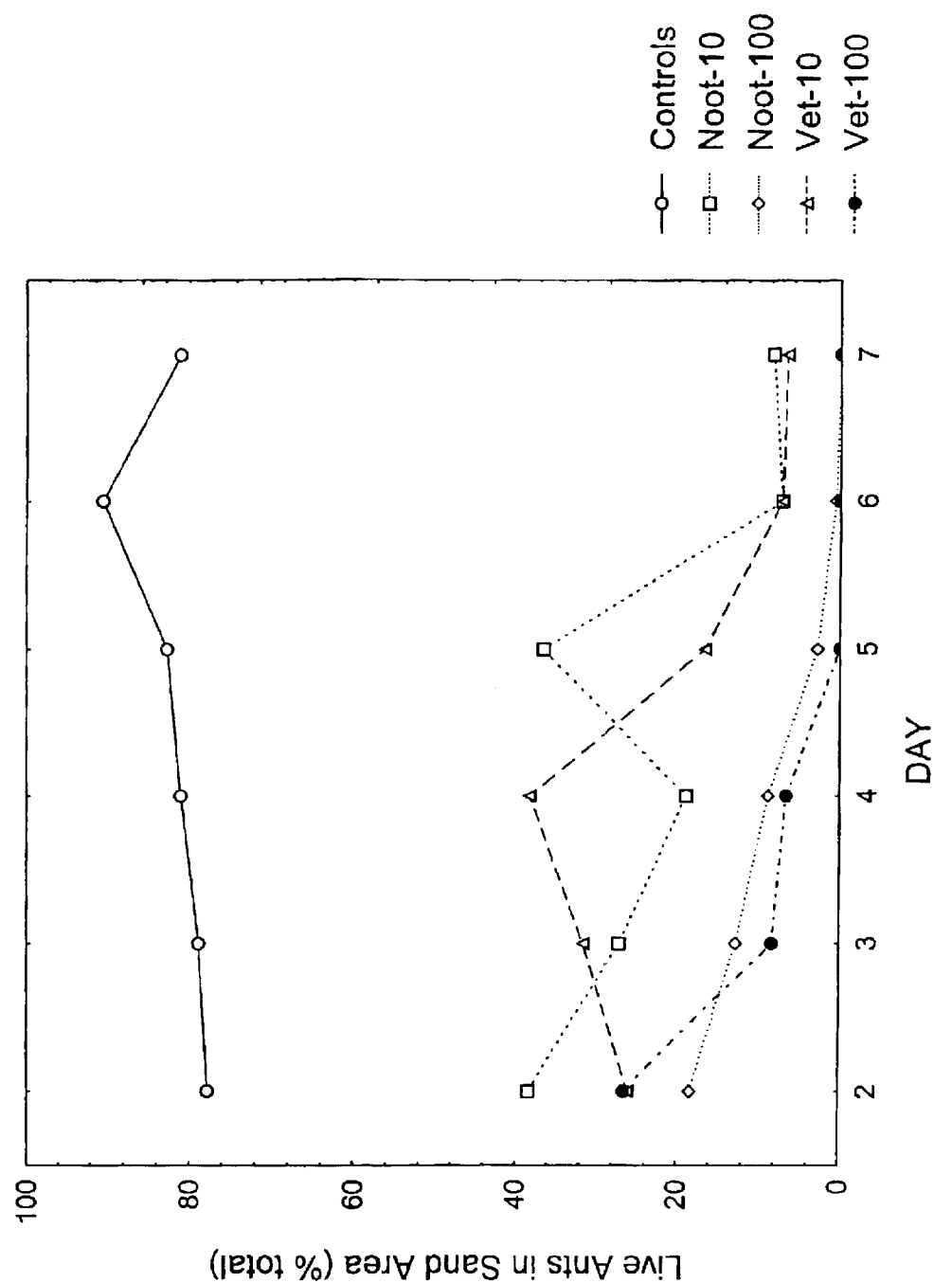
FIG. 1 illustrates the percent of living ants over seven days found in a sand area treated two hours prior to the experiment with the following different treatments: a control; 10 μg/g nootkatone ("Noot-10"), 100 μg/g nootkatone ("Noot-100"), 10 μg/g vetiver oil ("Vet-10") and 100 μg/g vetiver oil ("Vet-100").

Commercially available nootkatone was used to test for effectiveness as a toxicant or repellent to ants. Vetiver oil was also tested. We discovered that both nootkatone and vetiver oil are effective repellents and toxicants of fire ants (e.g., *Solenopsis invicta* Buren, Class Hexapoda, Order Hymenoptera) at concentrations as low as 10 μg/g. Both compositions reduced ant invasion and increased fire ant mortality.

Nootkatone was also shown to be an effective repellent and toxicant against ticks (e.g., *Ixodes scapularis*, Class Arachnida, Order Acari); and an effective repellent against cockroaches (e.g., *Blattella germanica*, Class Hexapoda and Order Blatteria).

Additionally, we believe that α-cedrene, a known component of vetiver oil, will also be an effective repellent of ants, ticks, and cockroaches, as will two additional extracts from vetiver oil: zizanol and bicyclovetivenol. All the above extracts have been shown to be effective repellents and toxicants of termites. (See WO 01/28343)

EXAMPLE 1

Ant Bio-activity of Nootkatone and Vetiver Oil

Nootkatone was purchased from a commercial source (Lancaster Synthesis Inc. Windham, N.H.). The source of the vetiver oil was The Good Scents Company (Oak Creek, Wis.). Three-chambered clear plastic containers (17×8×4 cm; Pioneer Packaging Co., North Dixon, Ky.) were used to test the effect of nootkatone and vetiver oil on the fire ants. Each rectangular container (17×8×4 cm) was divided into three equal compartments with two inner walls. A small hole (0.5 cm diameter) was melted at the bottom of each of the inner walls to permit fire ant access to all chambers. The top inner sides of the containers were coated with FLUON® (Northern Products, Inc., Woonsocket, R.I.) to prevent ants from escaping. Into the far left chamber, designated the "nest area," was placed a 55 mm #2 Whatman filter paper circle (Whatman International, Maidstone, England) moistened with 0.5 ml ddH$_2$O to serve as a substrate. For a food source, a second 55 mm #2 Whatman filter paper circle was moistened with 0.5 ml 10% sucrose solution and placed in the far right chamber ("feeding area"). In the middle chamber, 30 g of #4 fine blasting sand (Easy Crete, Inc., Greenwell Springs, La.) moistened with 3 ml ddH$_2$O was added. The sand had previously been treated by mixing with ethanol only (the controls) or with ethanol and solutions of nootkatone or vetiver oil to obtain final concentrations of 10 μg/g sand and 100 μg/g sand. The treated sand was allowed to air-dry for 2 hr in a ventilated hood before placing into the container.

Imported red fire ants, *Solenopsis invicta*, were collected the day before beginning the experiment from two Louisiana colonies (Colony A and Colony B) whose nests were 50 m apart. For each container, 30 workers were placed in the nest area in a small Petri dish (3.5 cm diameter) with the lid closed initially. The total number of containers was 30; 15 for each colony. For each colony, three replicates were established for each of the following treatments: a control; 10 μg/g nootkatone ("Noot-100"), 100 μg/g nootkatone ("Noot-100"), 10 μg/g vetiver oil ("Vet-10"), 10 μg/g vetiver oil ("Vet-100").

After the ants were acclimated, the lid on the Petri dish was removed. Ant behavior was observed during the first 15 min for the following: time for the first ant to cross into the middle chamber; time for the first ant to cross into the feeding area; and number of ants in the middle chamber after 5, 10, and 15 min. The plastic containers were kept closed with lids in a thermostatic chamber at 27° C. for one week. Each day at the same time, the numbers of live and dead ants in each chamber were noted.

To test for effectiveness of nootkatone and vetiver oil after the passage of time, the above experiment was repeated 40 days later with sand that had been treated at the same time as the above experiment. For 40 days, the sand had been maintained in separate chambers with non-hermetic lids in a dark room at room temperature. For this second experiment, fire ants were freshly collected from two different Louisiana colonies.

The number of ants, expressed as a percent of the total number in the container, found in the treated area after the first 15 minutes was compared using a two-way ANOVA followed by Newman-Keuls post-hoc test, considering the factors "colony" (A, B) and "treatment" (Control, Noot-100, Noot-10, Vet-100, Vet-10). Data for both the number of live and dead ants (expressed as percent of the total) during the seven days of the experiment were analyzed with 2-way ANOVA for repeated measures followed by Newman-Keuls post-hoc tests, considering the variables "colony" and "treatment" and the variable "day" as the repeated factor. All data were analyzed using Statistica 5.5 (1999 edition, Statsoft Inc., Tulsa, Okla.).

Immediately After Sand Treatment

As shown below, the percent of ants in the treated area was significantly different among treatments after 15 min ($F$=13.78, df=4,20; $P$<0.001), being higher for controls (Table 1). No significant differences between colonies were detected for the factor "colony" and the interactions "treatment x colony."

TABLE 1

Percent ants (% ± SE) in the sand area after 15 min.

| | Mean ± SE |
|---|---|
| Controls | 75.56 ± 3.33 a* |
| Noot-10 | 23.89 ± 3.35 b |
| Noot-100 | 13.33 ± 2.42 b |
| Vet-10 | 27.22 ± 2.33 b |
| Vet-100 | 33.33 ± 3.01 b |

*Means marked by the same letter are not significantly different at the 0.05 level determined by the Newman-Keuls test The percent of living ants found in the sand area over seven days was significantly different among the different treatments ($F$=322.41, df=4,20; $P$<0.001) and over the days ($F$=16.48, df=5,100; $P$<0.001), but was similar for the two colonies ($F$=1.26, df=1,20; $P$>0.05). The ants in the control containers were almost always found in the sand area, whereas substantially lower numbers of ants were found in sand with even the lowest concentration of vetiver oil or nootkatone. Almost no ants were found in sand treated with the highest concentration of either vetiver oil or nootkatone. (FIG. 1).

Figure 2:
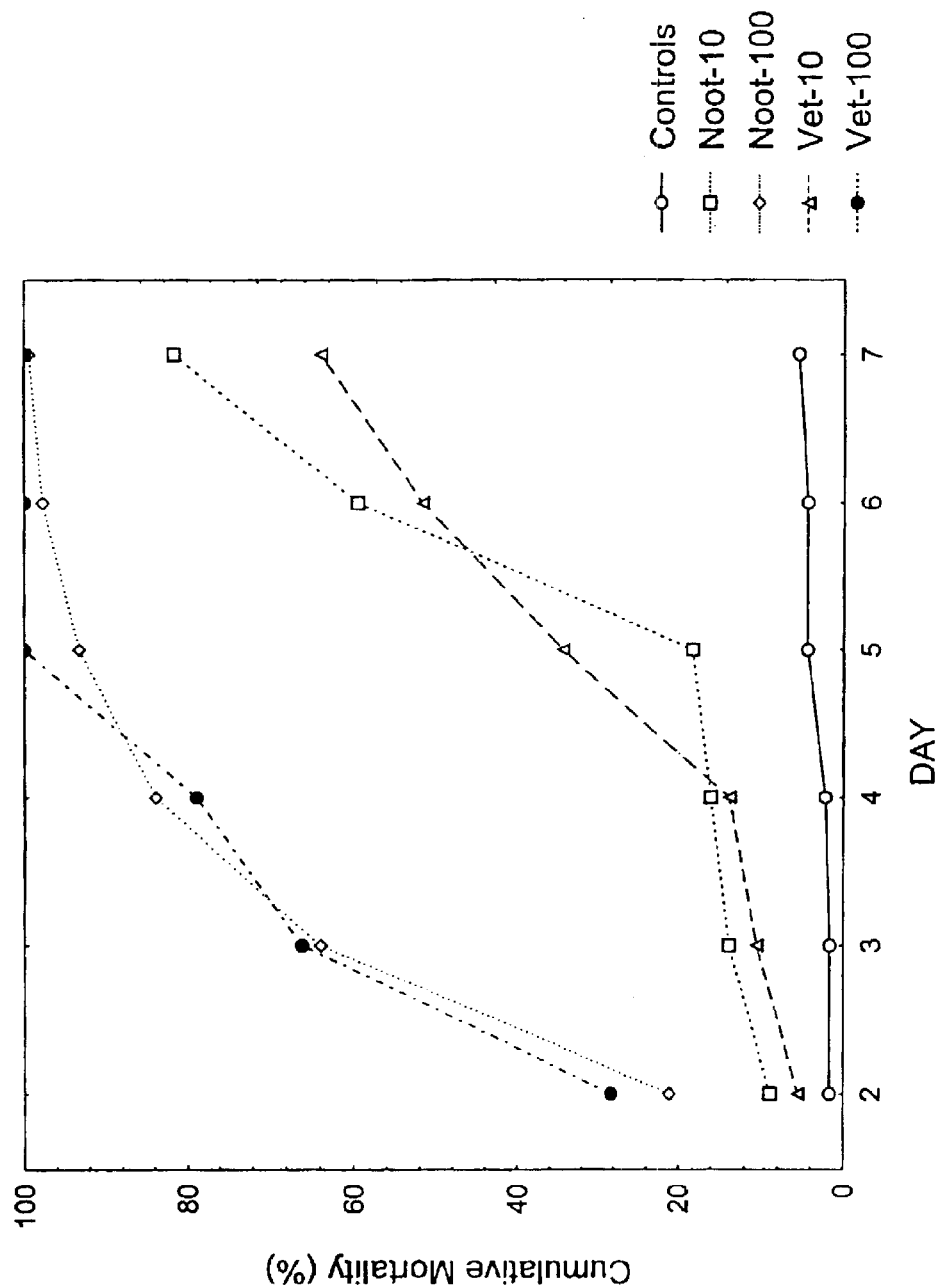
FIG. 2 illustrates the cumulative mortality over seven days of ants placed in containers with sand treated two hours prior to the experiment with the following different treatments: a control; 10 μg/g nootkatone ("Noot-10"), 100 μg/g nootkatone ("Noot-100"), 10 μg/g vetiver oil ("Vet-10"), and 10 μg/g vetiver oil ("Vet-100").

A significant difference was found in cumulative mortality over the 7 days among the various treatments ($F$=82.69, df=4,20; $P$<0.001). See FIG. 2. At any given time, mortality was highest in the containers with the highest concentration of vetiver oil or nootkatone. Overall mortality was less than 5% for the controls (FIG. 2). At any given time, a greater number of dead ants were found in the sand area for the treated containers.

Forty Days After Sand Treatment

The results of experiments using sand that had been treated forty days prior to the experiments were very similar to those reported above for sand treated only two hours prior to the experiments. After 15 min of adding the fire ants, the percent of ants in the sand area was significantly different among treatments ($\underline{F}$=9.30, df=4,20; $\underline{P}$<0.001). The number of ants in the sand area was significantly higher for controls (Table 2).

TABLE 2

Number of ants (% ± SE) in the sand area after 15 min (test after 40 days).

|  | Mean ± SE |
| --- | --- |
| Controls | 48.33 ± 2.46 a* |
| Noot-10 | 26.11 ± 3.07 b |
| Noot-100 | 13.89 ± 1.99 b |
| Vet-10 | 16.67 ± 2.67 b |
| Vet-100 | 15.00 ± 2.55 b |

Figure 3:
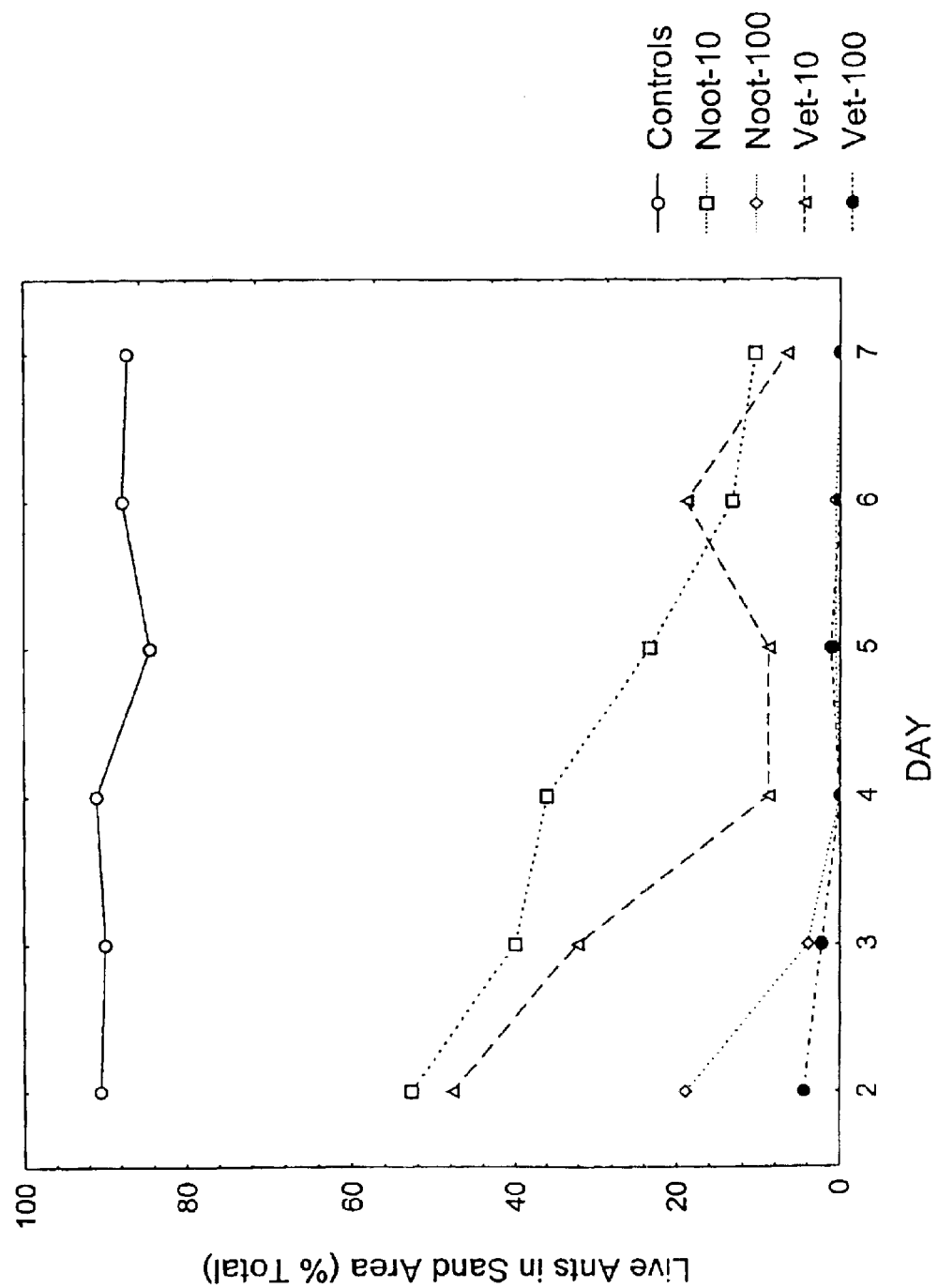
FIG. 3 illustrates the percentage of living ants over seven days found in a sand area treated forty days prior to the experiment with the following different treatments: a control; 10 μg/g nootkatone ("Noot-10"), 10 μg/g nootkatone ("Noot-100"), 100 μg/g vetiver oil ("Vet-10"), and 100 μg/g vetiver oil ("Vet-100").

*Means marked by the same letter are not significantly different at the 0.05 level determined by the Newman-Keuls test The percent of living ants found in the sand area over the next 7 days was significantly different among treatments ($\underline{F}$=181.82, df=4,20; $\underline{P}$<0.001) and over the days ($\underline{F}$=26.86, df=5,100; $\underline{P}$<0.001), but was similar for the two colonies ($\underline{F}$=3.83, df=1,20; $\underline{P}$>0.05). See FIG. 3. The ants in the control group were almost always found in the sand area; whereas significantly lower numbers of ants were found in sand treated with even the lowest concentration of vetiver oil or nootkatone. Almost no ants were found in sand treated with the highest concentration of either vetiver oil or nootkatone (FIG. 3).

Figure 4:
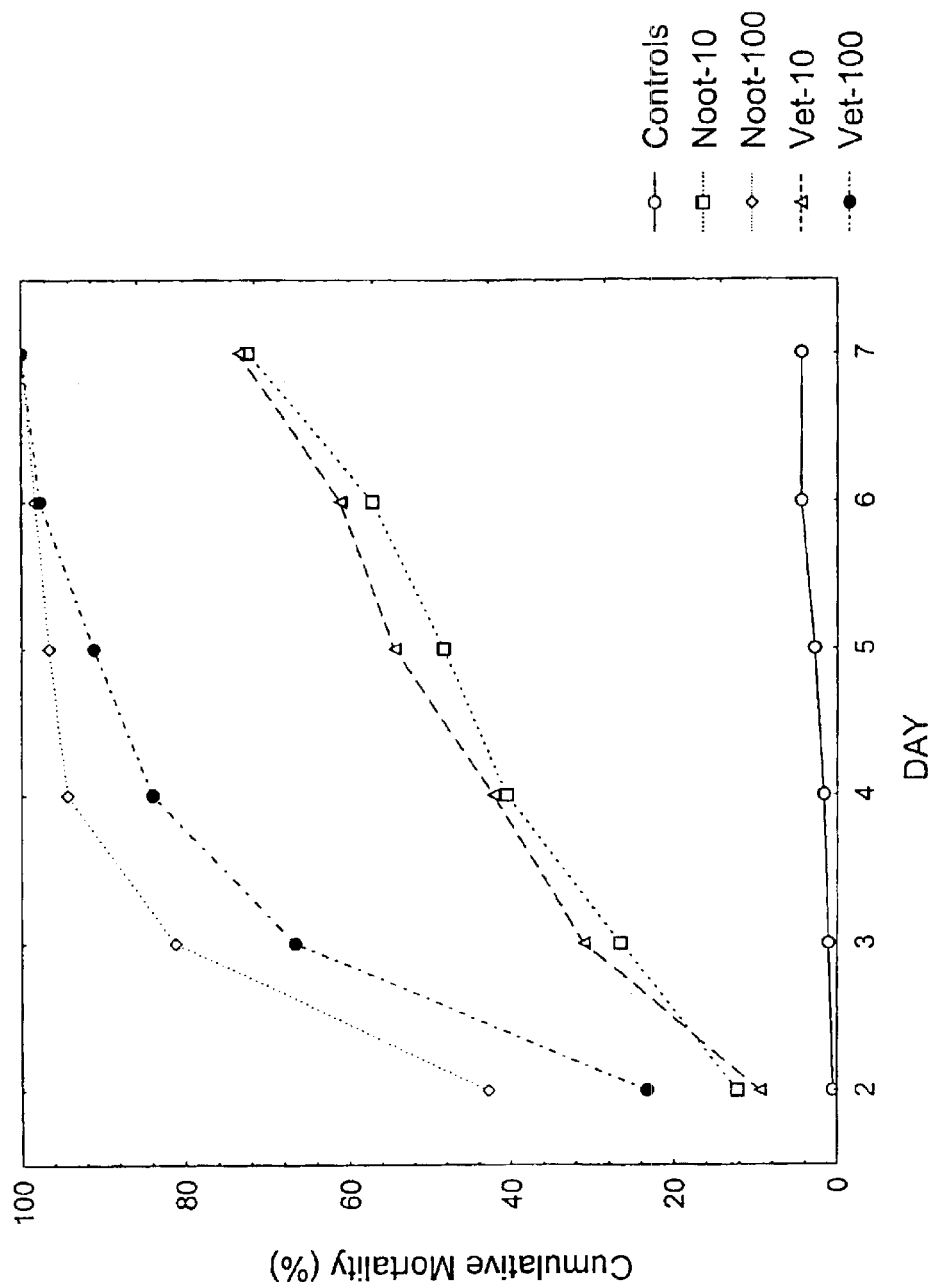
FIG. 4 illustrates the cumulative mortality over seven days of ants placed in containers with sand treated forty days prior to the experiment with the following different treatments: a control; 10 μg/g nootkatone ("Noot-10"), 100 μg/g nootkatone ("Noot-100"), 10 μg/g vetiver oil ("Vet-10"), and 100 μg/g vetiver oil ("Vet-100").

A significant difference was also found in the cumulative mortality among different treatments over the next 7 days ($\underline{F}$=73.39, df=4,20; $\underline{P}$<0.001). See FIG. 4. Cumulative mortality was always greatest in the containers with the highest concentration of vetiver oil or nootkatone, significantly lower in the lower concentration of either, and was insubstantial for the controls (FIG. 4). The greatest number of dead ants were found in the sand area of the treated containers.

These results show that nootkatone and vetiver oil at concentrations as low as 10 $\mu$g/g decreased ant invasion and increased ant mortality. Nootkatone and vetiver oil were shown to be potent fire ant repellents and toxicants. It is believed that concentrations between 10 $\mu$g/g and 1000 $\mu$g/g, more preferably between 10 $\mu$g/g and 200 $\mu$g/g, will be useful in repelling and killing fire ants. Moreover, both nootkatone and vetiver oil were still effective forty days after the initial application.

EXAMPLE 2

Ant Bio-activity of α-Cedrene

The fire ant bio-activity of α-cedrene, a component of vetiver oil, will be tested using a commercially available product (Fluka, a division of Sigma-Aldrich, Inc., St. Louis, Mo.). A new method for screening compounds will be used that is faster than the bioassay described in Example 1. Five cm diameter Petri dishes with lids will be used. Two ml of hot agar solution (1.5 gm/100 ml ddH$_2$O) will be spread evenly in the bottom of each dish and allowed to cool. The agar solution will provide moisture for the fire ants and hold the sand in place. The sand will be autoclaved for 30 min before adding either ethanol alone or ethanol with sample. Then the sand will be dried in an oven. For three dishes, one half of the bottom of each dish will be covered with 1.5 gm sand previously mixed with a total of 100 $\mu$g (or other amounts) α-cedrene per dish, dissolved in ethanol, and the other half with 1.5 gm untreated sand (only ethanol). The sand will completely cover the agar, but will not be thick enough to conceal the fire ants. Three dishes will be prepared as controls with only untreated sand in each side. Finally, ten fire ants will be added to each dish, and the dishes covered to eliminate light.

The fire ant distribution in each dish, measured by counting the number of fire ants on the untreated half of the dish, will be examined each hour for up to 8 hr. When 70% or more of the fire ants (in at least three replicates) are observed on the untreated sand, the sample will be considered to have activity as a repellent. Also, the number of fire ants that are normal, ataxic, moribund or dead will be recorded.

It is believed that α-cedrene will be a repellent for fire ants, at least in the 2–3 hr time frame.

EXAMPLE 3

Ant Bio-activity of Vetiver Oil Extracts Comprising Zizanol and Bicyclovetivenol Extracts of Louisiana grown vetiver oil were prepared as described in international application, PCT/US00/29006 (Published as WO 01/28343), using a silica gel column and TLC. Fractions with high bio-activity were analyzed with GC-MS and found to have high concentrations of zizanol and bicyclovetivenol. From this information, extracts with higher concentrations of zizanol and bicyclovetivenol, both together and individually, will be prepared and analyzed for fire ant bio-activity using the quick Petri dish method as described in Example 2.

It is believed that both zizanol and bicyclovetivenol, individually as well as together, will show fire ant activity as repellents.

EXAMPLE 4

Toxicity of Nootkatone

To further determine the level of toxicity of nootkatone on ants, a toxicity experiment will be conducted. Fire ants will be placed in sealed containers that contain a sand substrate. In three sets of containers the sand will be treated with nootkatone at levels of 110 $\mu$g/g, 100 $\mu$g/g, and 200 $\mu$g/g of sand, respectively. The fourth container will be a control with no nootkatone. Daily counts of dead fire ants over a one-week period will be made to determine mortality for each treatment. Based on these results, a dose-response curve will be generated.

EXAMPLE 5

Repellency and Toxicity of Diatomaceous Earth or Soil Treated with Nootkatone

To demonstrate the effectiveness of nootkatone in repelling ants from a different substrate, experiments will be conducted as described in Example 1 using, instead of the sand, diatomaceous earth or soil treated with various concentrations of nootkatone.

EXAMPLE 6

Repellency and Toxicity of Nootkatone Against Ticks

To test the effectiveness of nootkatone against ticks, ticks (*Ixodes scapularis*) were collected from Idlewild, La. Nootkatone efficiacy was tested relative to a known repellent, N,N-diethyl-m-toluamide ("Deet"). REPEL®, which contains 27.55% Deet, was purchased locally from a retail garden store.

The bioassay was conducted using Petri dishes (5 cm diameter and 1 cm height). To ensure adequate moisture for the ticks, 1 ml of a hot agar solution (1.5% in $H_2O$) was spread evenly on the inside surfaces of the Petri dish, including the top, bottom, and edges. After the agar cooled, sand that was treated as described below was spread evenly on the inside surfaces of the Petri dish. The sand was held in place by the agar.

For the treated sand, either 2 mg nootkatone or 100 mg REPEL® was initially dissolved in 2 ml ethanol, and then 200 µl of the solution was mixed with 2 g sand that had been autoclaved and cooled. The control was autoclaved sand with 200 µl ethanol only added. One half of the surfaces in the Petri dishes were covered with 2 g treated sand, and the other half with 2 g untreated sand. In the nootkatone-treated Petri dishes, the final concentration was 200 µg/dish; while in the Deet treated Petri dishes, the final concentration was 2.75 mg/dish. Control Petri dishes were prepared by covering all sides with untreated sand. One tick was added to each Petri dish, and the top replaced. The number of replicates were as follows: control, 6; nootkatone, 9; and Deet, 8. The Petri dishes were checked at 15 min, 30 min, 1 hr, 2 hr, 3 hr, 4 hr, 5 hr, 6 hr, 68 hr, and 90 hr. Repellent activity was noted if the tick was found on the untreated side of the Petri dish. The ticks in the control Petri dishes were randomly distributed on the left and right sides.

All Petri dishes treated with either nootkatone or Deet showed repellent activity to ticks at 15 min, and that activity remained up to 68 hr (i.e., all ticks in the treated dishes were found on the untreated side of the dish). After 90 hr, three Petri dishes treated with Deet had lost the repellent activity. After 90 hr, four ticks (50%) in the nootkatone-treated Petri dishes were dead. No ticks in the other treatments died.

The above experiment was repeated with ticks (*Ix. scapularis*) collected from Hammond, La. The number of replicates in this experiment were as follows: controls, 8; nootkatone, 10; and Deet, 8. In this experiment, the Petri dishes were observed at 15 min, 30 min, 1 hr, 2 hr, 3 hr, 4 hr, 24 hr, 48 hr, 72 hr, and 96 hr.

All Petri dishes treated with either nootkatone or Deet retained repellent activity up to 72 hr. After 96 hr, one Petri dish treated with Deet lost the repellent activity. At 24 hr, one tick had died in both a nootkatone dish and a Deet Petri dish. At 72 hr, four ticks (40%) had died in the nootkatone dishes, while only one in the Deet. At 96 hr, nine ticks (90%) had died in the nootkatone dishes, while only four (50%) had died in the Deet dishes.

These results indicate that nootkatone is an effective repellent and toxicant against ticks. Nootkatone was shown to maintain its repellent activity longer than Deet, and to be a stronger toxicant than Deet. In a similar manner, the effectiveness of α-cedrene, zizanol, and bicyclovetivenol will be tested against ticks.

EXAMPLE 7

Effectiveness of Nootkatone Against the Cat Flea

To test the effectiveness of nootkatone against fleas, cat fleas (*Ctenocephalides felis* (Bouche)) were collected from a flea colony at St. Gabriel, La.

Petri dishes (5 cm diameter and 1 cm height) were prepared by lining one half of the top and the bottom with a half circle of filter paper (55 mm), and lining the other half with a second half circle of filter paper. For the treated Petri dishes, 50 mg nootkatone or 100 mg REPEL® were dissolved in 0.5 ml ethanol. To each Petri dish was added either ethanol only, 2.75 mg Deet, 0.2 mg nootkatone, 1 mg nootkatone, or 2 mg nootkatone. Ten replicate Petri dishes were used for each of the treatments. The ethanol solution was added to the filter paper on the top and bottom and dried for 10 min. To place the fleas in the Petri dishes, fleas were temporarily immobilized by placing them at −20° C. for 5 min. The number of fleas in each Petri dish varied: for the 10 control Petri dishes, the average number in each dish was 10.2, with a range of 4 to 23; for 0.2 mg nootkatone, the average number in each dish was 8.5, with a range of 5 to 18; for 1 mg nootkatone, the average number in each dish was 10.6, with a range of 6 to 21; for 2 mg nootkatone, the average number in each dish was 11.1, with a range of 9 to 15 (Fleas could be counted in only 9 Petri dishes; one had too many fleas to count); and for 2.76 mg Deet, the average number in each dish was 6.7, with a range of 5 to 9.

The number of fleas on each side of each Petri dish was counted at 1 hr, 2 hr, 3 hr, 4 hr, 24 hr, 48 hr, 72 hr, and 96 hr.

Although Deet showed repellent activity at the first observation (1 hr), none of the concentrations of nootkatone indicated any repellent activity against the fleas. In the Deet dishes, 50% of the fleas were dead at 4 hr; and 100% at 24 hr. See Table 3. For 0.2 mg nootkatone, 22% of the fleas were dead at 24 hr; and 79% were dead at the last observation, 96 hr. For 1 mg nootkatone, 16% fleas were dead at 3 hr; and 98% dead at 96 hr. Finally, for 2 mg nootkatone, 26% fleas were dead at 3 hr; and 94% dead at 96 hr. See Table 3.

TABLE 3

Summary of Percent Flea Mortality

| Treatment | 1 hr | 2 hr | 3 hr | 4 hr | 24 hr | 48 hr | 72 hr | 96 hr |
|---|---|---|---|---|---|---|---|---|
| Control | 0% | 0% | 0% | 0% | 9% | 20% | 43% | 54% |
| 2.76 mg Deet | 0% | 0% | 0% | 49% | 100% | 100% | 100% | 100% |
| 0.2 mg nootkatone | 0% | 0% | 0% | 0% | 22% | 45% | 72% | 79% |
| 1 mg nootkatone | 0% | 0% | 16% | 38% | 66% | 92% | 89% | 98% |
| 2 mg nootkatone | 0% | 0% | 26% | 50% | 77% | 84% | 91% | 94% |

Thus, although Deet was shown to be effective as both a repellent and a toxicant, nootkatone showed no repellent activity against fleas and only delayed toxicant activity. Deet killed all fleas by 24 hr; the highest level nootkatone (2 mg) killed only 94% of the fleas by 96 hr.

Unlike termites, fire ants, and ticks, fleas are not repelled by nootkatone; and are only killed after a delayed exposure. This experiment demonstrates the uniqueness of each insect group in their sensitivity to different chemicals and the need to test the insect group to determine the effectiveness of any specific chemical.

EXAMPLE 8

Effectiveness of Nootkatone Against Cockroaches

To test the efficacy of nootkatone against cockroaches, German cockroaches (*Blattella germanica*) were collected at Baton Rouge, La., the same day as the bioassay was begun.

For the bioassay, Petri dishes (10 cm diameter×1 cm) were used. The Petri dishes were prepared by lining one half of the top and one half of the bottom with a half circle of filter paper (125 mm), and lining the other half with a second half circle of filter paper. For the treated Petri dishes, 50 mg nootkatone and 300 mg REPEL® were dissolved in 2.0 ml ethanol. To each Petri dish was added either ethanol only, 30 mg Deet, 1 mg nootkatone, or 10 mg nootkatone. Ten replicate Petri dishes were used for each of the treatments. The ethanol solution was added to the filter paper on the top and bottom and dried for 10 min. One cockroach was added to each Petri dish. The length of the cockroaches varied from 1 to 1.5 cm. The dishes were then observed at 15 min, 30 min, 1 hr, 2 hr, 3 hr, 4 hr, 5 hr, 24 hr, 48 hr, and 120 hr.

As shown below in Table 4, Deet had no significant repellent activity against the cockroaches. In contrast, even 1 mg nootkatone was a weak repellent. At 10 mg nootkatone, 100% repellency was observed after 1 hr, which remained until 120 hr. The number of cockroach deaths was not significantly different from the control for any of the treatments. Thus neither Deet nor nootkatone was shown to be a toxicant to cockroaches. In a similar manner, the effectiveness of α-cedrene, zizanol, and bicyclovetivenol will be tested against cockroaches.

compared to the activity or viability in an otherwise identical environment without the added compound or composition. Statistical significance is determined at $p<0.05$.

The complete disclosures of all references cited in this specification are hereby incorporated by reference. Also incorporated by reference are the complete disclosures of the following publication and unpublished manuscripts: B. Zhu et al., "Nootkatone is a repellent for Formosan subterranean termites (*Coptotermes foirmosanus*;" Journal of Chemical Ecology, vol. 27, pp. 523–531 (2001); L. Maistrello et al., "Effects of nootkatone and a borate compound on Formosan subterranean termite and its symbiont protozoa," submitted to Journal of Entomological Science (2001); and B. Zhu et al., "Evaluation of vetiver oil and seven insect-active essential oils against Formosan subterranean termites," Journal of Chemical Ecology, vol. 27, pp. 1617–1625 (2001); L. Maistrello et al., "Effects of vetiver oil and its consitutents on *Coptotermes formosanus* and its symbiotic fauna," poster presentation at XXI International Congress of Entomology, Iguassu Falls, Brazil, Aug. 20–26, 2000; and the complete text of U.S. provisional patent application Ser. No. 60/160,251, filed Oct. 19, 1999. In the event of an otherwise irreconcilable conflict, however, the present specification shall control.

We claim:

1. A method for protecting a material from ant infestation, comprising treating the material with an effective amount of a compound selected from the group consisting of α-cedrene, zizanol, and bicyclovetivenol, wherein the treated material repels or kills ants substantially more than does an otherwise identical material that has not been treated with the compound.

2. A method as in claim 1, wherein the ants are fire ants.

3. A method as in claim 1, wherein the treated material repels ants.

4. A method as in claim 1, wherein the treated material kills ants.

5. A method as in claim 1, wherein the material is selected from the group consisting of soil, synthetic polymers, diatomaceous earth, sand, and cellulose-containing materials.

6. A method as in claim 1, wherein the compound is α-cedrene.

7. A method as in claim 1, wherein the compound is zizanol.

TABLE 4

Summary of Percent Repellency at Various Observation Times

| Treatment | 30 min | 1 hr | 2 hr | 3 hr | 4 hr | 5 hr | 24 hr | 48 hr | 120 hr |
|---|---|---|---|---|---|---|---|---|---|
| 30 mg Deet | 50% | 40% | 70% | 50% | 60% | 70% | 38% | 43% | 50% |
| 1 mg nootkatone | 70% | 60% | 50% | 78% | 78% | 78% | 56% | 78% | 100% |
| 10 mg nootkatone | 90% | 100% | 100% | 100% | 100% | 100% | 100% | 100% | 100% |

In the specification and the claims, an "effective amount" of a compound or composition, e.g., nootkatone, α-cedrene, or zizanol and bicyclovetivenol, is defined to be an amount that, when applied to a substrate or other material, causes statistically significant repellence or toxicity, or that significantly decreases the activity or viability of arthropods, as 8. A method as in claim 1, wherein the compound is bicyclovetivenol.

9. A method as in claim 1, additionally comprising treating the material with one or more additional, different compounds selected from the group consisting of nootkatone, α-cedrene, zizanol, and bicyclovetivenol.

10. A method for protecting a material from ant infestation, comprising treating the material with an effective amount of nootkatone, wherein the treated material repels ants substantially more than does an otherwise identical material that has not been treated with nootkatone.

11. A method as in claim 10, wherein the ants are fire ants.

12. A method as in claim 10, wherein the material is selected from the group consisting of soil, synthetic polymers, diatomaceous earth, sand, and cellulose-containing materials.

* * * * *